(12) United States Patent
Liu et al.

(10) Patent No.: US 7,725,185 B2
(45) Date of Patent: *May 25, 2010

(54) CARDIAC STIMULATION AT HIGH VENTRICULAR WALL STRESS AREAS

(75) Inventors: Lili Liu, St. Paul, MN (US); Rodney Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 113 days.

This patent is subject to a terminal disclaimer.

(21) Appl. No.: 12/070,080

(22) Filed: Feb. 15, 2008

(65) Prior Publication Data

US 2008/0140144 A1 Jun. 12, 2008

Related U.S. Application Data

(63) Continuation of application No. 10/952,346, filed on Sep. 28, 2004, now Pat. No. 7,346,394, which is a continuation-in-part of application No. 10/649,468, filed on Aug. 27, 2003, now Pat. No. 7,103,410, which is a continuation of application No. 09/844,256, filed on Apr. 27, 2001, now Pat. No. 6,628,988.

(51) Int. Cl.
*A61N 1/365* (2006.01)
*A61N 1/05* (2006.01)

(52) U.S. Cl. .............................. 607/17; 607/9; 607/11; 607/18

(58) Field of Classification Search ..................... 607/17
See application file for complete search history.

(56) References Cited

U.S. PATENT DOCUMENTS

| 4,354,497 | A | 10/1982 | Kahn |
| 4,549,548 | A | 10/1985 | Wittkampf et al. |
| 4,554,922 | A | 11/1985 | Prystowsky et al. |
| 4,628,934 | A | 12/1986 | Pohndorf et al. |
| 4,674,518 | A | 6/1987 | Salo |
| 4,928,688 | A | 5/1990 | Mower |

(Continued)

FOREIGN PATENT DOCUMENTS

EP 0522693 1/1993

(Continued)

OTHER PUBLICATIONS

Braunwald et al., Sustained Paired Electrical Stimuli; Slowing of the Ventricular Rate and Augmentation of Contractile Force, *American Journal of Cardiology 14* (1964) pp. 285 & 385-393.

(Continued)

*Primary Examiner*—Mark W Bockelman
*Assistant Examiner*—Elizabeth K So
(74) *Attorney, Agent, or Firm*—Hollingsworth & Funk, LLC

(57) ABSTRACT

An apparatus and method for reversing ventricular remodeling with electro-stimulatory therapy. A ventricle is paced by delivering one or more stimulatory pulses in a manner such that a stressed region of the myocardium is pre-excited relative to other regions in order to subject the stressed region to a lessened preload and afterload during systole. The unloading of the stressed myocardium over time effects reversal of undesirable ventricular remodeling.

21 Claims, 7 Drawing Sheets

U.S. PATENT DOCUMENTS

| | | | |
|---|---|---|---|
| 5,058,605 A | 10/1991 | Slovak |
| 5,156,149 A | 10/1992 | Hudrlik |
| 5,174,289 A | 12/1992 | Cohen |
| 5,233,985 A | 8/1993 | Hudrlik |
| 5,267,560 A | 12/1993 | Cohen |
| 5,334,222 A | 8/1994 | Salo et al. |
| 5,370,665 A | 12/1994 | Hudrlik |
| 5,423,883 A | 6/1995 | Helland |
| 5,514,161 A | 5/1996 | Limousin |
| 5,549,652 A | 8/1996 | McClure et al. |
| 5,584,867 A | 12/1996 | Limousin et al. |
| 5,628,777 A | 5/1997 | Moberg et al. |
| 5,674,259 A | 10/1997 | Gray |
| 5,738,096 A | 4/1998 | Ben-Haim |
| 5,792,203 A | 8/1998 | Schroeppel |
| 5,797,970 A | 8/1998 | Pouvreau |
| 5,935,160 A | 8/1999 | Auricchio et al. |
| 5,941,904 A | 8/1999 | Johnston et al. |
| 5,995,870 A | 11/1999 | Cazeau et al. |
| 5,995,871 A | 11/1999 | Knisley |
| 6,002,963 A | 12/1999 | Mouchawar et al. |
| 6,009,349 A | 12/1999 | Mouchawar et al. |
| 6,026,320 A | 2/2000 | Carlson et al. |
| 6,223,082 B1 | 4/2001 | Bakels et al. |
| 6,263,241 B1 | 7/2001 | Rosborough et al. |
| 6,278,894 B1 | 8/2001 | Salo et al. |
| 6,285,907 B1 | 9/2001 | Kramer et al. |
| 6,314,322 B1 | 11/2001 | Rosenberg |
| 6,363,278 B1 | 3/2002 | Stahmann et al. |
| 6,363,279 B1 | 3/2002 | Ben-Haim et al. |
| 6,366,811 B1 | 4/2002 | Carlson |
| 6,371,922 B1 | 4/2002 | Baumann et al. |
| 6,411,848 B2 | 6/2002 | Kramer et al. |
| 6,424,865 B1 | 7/2002 | Ding |
| 6,459,929 B1 | 10/2002 | Hopper et al. |
| 6,501,998 B1 | 12/2002 | Pfeiffer |
| 6,512,952 B2 | 1/2003 | Stahmann et al. |
| 6,542,775 B2 | 4/2003 | Ding et al. |
| 6,556,872 B2 | 4/2003 | Hauck |
| 6,564,094 B2 | 5/2003 | Alferness et al. |
| 6,574,506 B2 | 6/2003 | Kramer et al. |
| 6,589,160 B2 | 7/2003 | Schweich, Jr. et al. |
| 6,597,951 B2 | 7/2003 | Kramer |
| 6,628,988 B2 | 9/2003 | Kramer et al. |
| 6,629,921 B1 | 10/2003 | Schweich, Jr. et al. |
| 6,640,135 B1 | 10/2003 | Salo et al. |
| 6,650,940 B1 | 11/2003 | Zhu et al. |
| 6,856,836 B2 | 2/2005 | Ding et al. |
| 6,915,149 B2 | 7/2005 | Ben-Haim |
| 6,973,349 B2 | 12/2005 | Salo |
| 7,450,988 B2 | 11/2008 | Ross et al. |
| 2004/0172078 A1 | 9/2004 | Chinchoy |
| 2005/0177195 A1 | 8/2005 | Salo |

FOREIGN PATENT DOCUMENTS

| | | |
|---|---|---|
| WO | WO0009206 | 2/2000 |
| WO | WO03037428 | 5/2003 |
| WO | WO2004008955 | 1/2004 |
| WO | WO2004024229 | 3/2004 |

OTHER PUBLICATIONS

Sabbah et al., Delivery of Non-Excitatory Contractibility—Modulation Electric Signals Improve left Ventricular Performance in Dogs with heart Failure, *Circulation*, Supplement 1, 100 (18). Abstract No. 631 (Nov. 2, 1999) pp. 1-122.

Sutton et al., The Foundations of Cardiac Pacing—Part 1, Chapter 9—Techniques of Implantation, Sections 9.4-9.6, p. 187-206, Futura Publishing Company, Inc.

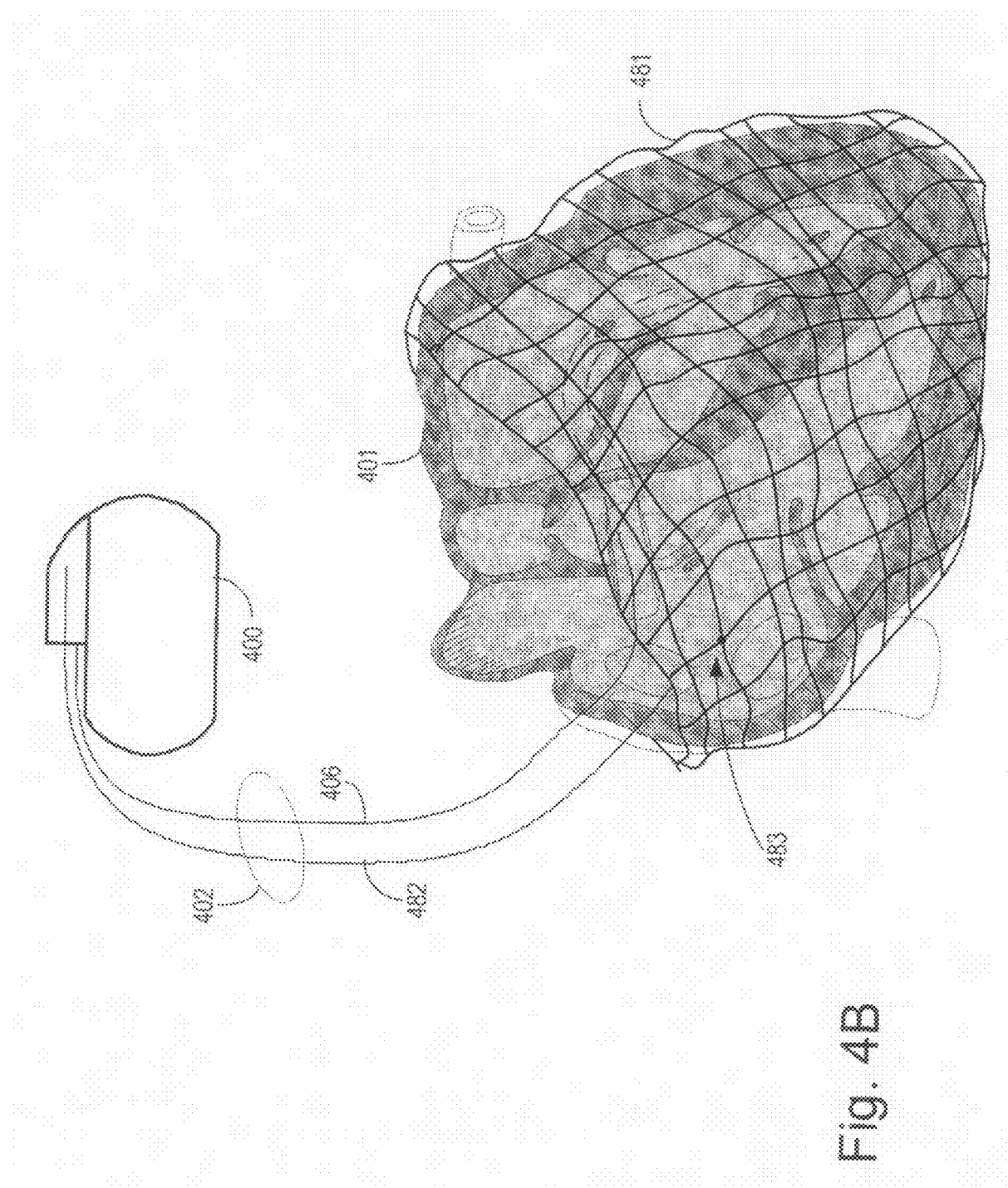

CARDIAC STIMULATION AT HIGH VENTRICULAR WALL STRESS AREAS

RELATED APPLICATIONS

This application is a continuation of U.S. patent application Ser. No. 10/952,346, filed on Sep. 28, 2004, now issued as U.S. Pat. No. 7,346,394, which is a continuation-in-part of U.S. patent application Ser. No. 10/649,468, filed on Aug. 27, 2003, now issued as U.S. Pat. No. 7,103,410, which is a continuation of U.S. patent application Ser. No. 09/844,256, filed on Apr. 27, 2001, now issued as U.S. Pat. No. 6,628,988 and which are hereby incorporated herein by reference.

FIELD OF THE INVENTION

The present invention relates generally to medical devices and, more particularly, to implantable cardiac stimulation therapy devices and methods of cardiac stimulation therapy.

BACKGROUND OF THE INVENTION

Congestive heart failure (CHF) is a clinical syndrome in which an abnormality of cardiac function causes cardiac output to fall below a level adequate to meet the metabolic demand of peripheral tissues. CHF can be due to a variety of etiologies with that due to ischemic heart disease being the most common. Inadequate pumping of blood into the arterial system by the heart is sometimes referred to as "forward failure," with "backward failure" referring to the resulting elevated pressures in the lungs and systemic veins which lead to congestion.

Backward failure is the natural consequence of forward failure as blood in the pulmonary and venous systems fails to be pumped out. Forward failure can be caused by impaired contractility of the ventricles or by an increased afterload (i.e., the forces resisting ejection of blood) due to, for example, systemic hypertension or valvular dysfunction.

One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism, but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium, which leads to alterations in cellular structure, a process referred to as ventricular remodeling.

Hypertrophy can increase systolic pressures but also decreases the compliance of the ventricles and hence increases diastolic filling pressure to result in even more congestion. It also has been shown that the sustained stresses causing hypertrophy may induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the process ultimately results in both systolic and diastolic dysfunction. It has been shown that the extent of ventricular remodeling is positively correlated with increased mortality in CHF patients.

SUMMARY OF THE INVENTION

The present invention relates to devices and method for reversing ventricular remodeling with electro-stimulatory therapy. In accordance with embodiments of the present invention, a ventricle is paced by delivering one or more stimulatory pulses in a manner such that a previously stressed and remodeled region of the myocardium is pre-excited relative to other regions in order to reverse the tissue remodeling.

A method of cardiac remodeling reversal in accordance with the present invention involves accessing a patient's heart, and detecting, proximate the heart wall, a target region having a level of abnormal wall motion relative to neighboring regions. An electrode may be implanted near the target region. The target region is pre-excited relative to the neighboring regions of the heart wall using the electrode in order to alter stress at the target region for treating cardiac remodeling.

Heart wall motion may be detected using, for example, an acceleration measurement, a strain measurement, and/or an ultrasonic velocity measurement such as a local Doppler tissue velocity measurement. The electrode may be used to pre-excite the target region in response to an atrial sense, an atrial pace, a ventricular sense or pace event, or other timing event or methodology. The remodeling reversal pre-excitation may be adjusted in accordance with activity level measurements reflective of metabolic demand. Detecting the target region of the heart may involve sensing activation characteristics of heart wall tissue, such as one or more electrophysiologic characteristics, complex impedance characteristics, or other characteristics of the heart wall tissue indicative of remodeling.

The pulse output sequence best suited for reversal of remodeling may not be the optimum pulse output sequence for maximizing hemodynamic performance. In another embodiment, therefore, the pulse output sequence is adjusted automatically in accordance with activity level measurements reflective of metabolic demand. The pulse output sequence is then alternated between one designed to produce more hemodynamically-effective contractions when metabolic needs of the body are great to one designed for remodeling reversal when metabolic needs are less.

A cardiac system suitable for cardiac remodeling reversal in accordance with the present invention includes an implantable housing having a controller configured to control cardiac monitoring and stimulation. Detection circuitry and energy delivery circuitry are provided in the housing and coupled to the controller. A lead is coupled to the detection circuitry and the energy delivery circuitry. The lead includes a lead body with at least one cardiac electrode and at least one sensor supported by the lead body and configured to detect abnormal cardiac wall motion. The sensor provides information useful for positioning the cardiac electrode proximate a target heart wall location associated with increased stress relative to neighboring heart wall locations. The sensor may be situated at a distal region of the lead, or the cardiac electrode may be situated at a distal end of the lead, and the sensor situated proximal of the cardiac electrode.

Embodiments of a device in accordance with the present invention may include leads having a fixation arrangement configured to fix the lead at the target heart wall location. Further embodiments include an activity sensor situated in or on the housing and coupled to the controller, wherein the controller is programmed to adjust a pacing therapy in response to signals indicative of metabolic demand received from the activity sensor.

The above summary of the present invention is not intended to describe each embodiment or every implementation of the present invention. Advantages and attainments, together with a more complete understanding of the invention, will become apparent and appreciated by referring to the following and claims taken in conjunction with the accompanying drawings.

BRIEF DESCRIPTION OF THE DRAWINGS

FIG. 4B is an illustration of an implantable cardiac device including a mesh configured for local stress measurements, the device configured for ventricular wall remodeling reversal in accordance with embodiments of the present invention;

Figure 1:
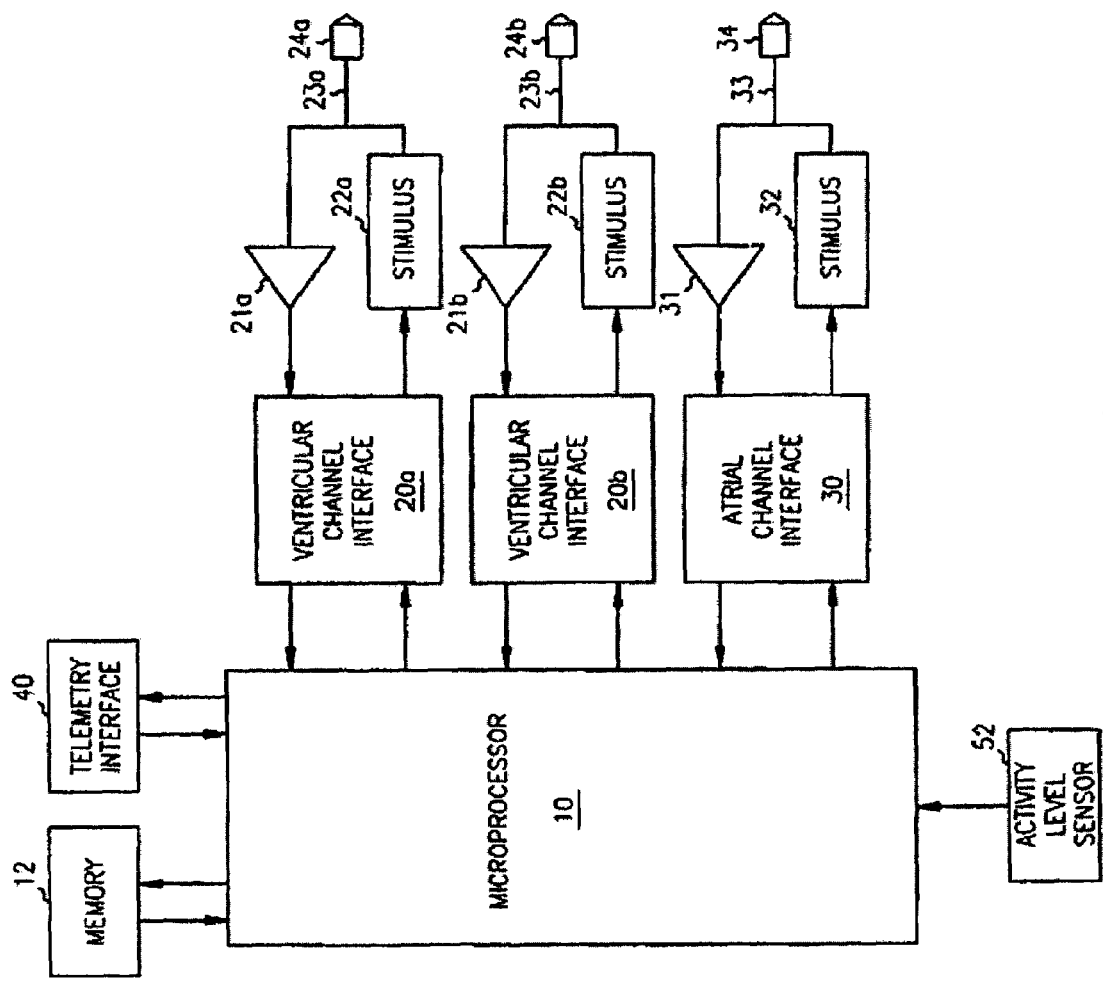
FIG. 1 is a block diagram of an example of a cardiac rhythm management device in accordance with present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION

A device employing cardiac stimulation methods and devices in accordance with the present invention may incorporate one or more of the features, structures, methods, or combinations thereof described herein below. For example, a cardiac monitor or stimulator and cardiac implantation devices may be implemented to include one or more of the advantageous features and/or processes described below. It is intended that such devices or methods need not include all of the features and functions described herein, but may be implemented to include selected features and functions that, in combination, provide for unique structures and/or functionality.

Conventional cardiac pacing with implanted pacemakers involves excitatory electrical stimulation to the heart by use of an electrode in electrical contact with the myocardium. As the term is used herein, "excitatory stimulation" refers to stimulation sufficient to cause contraction of muscle fibers, which is also commonly referred to as pacing. Furthermore, the term "pacemaker" should be taken to mean any cardiac rhythm management device with a pacing functionality, regardless of any other functions it may perform such as cardioversion/defibrillation or drug delivery. A pacemaker is usually implanted subcutaneously on the patient's chest, and is typically connected to an electrode for each paced heart chamber by leads threaded through the vessels of the upper venous system into the heart, and/or placed epicardially. In response to sensed electrical cardiac events and elapsed time intervals, the pacemaker delivers to the myocardium a depolarizing voltage pulse of sufficient magnitude and duration to cause an action potential. A wave of depolarizing excitation then propagates through the myocardium, resulting in a heartbeat.

Various forms of cardiac pacing can often benefit CHF patients. For example, sinus node dysfunction resulting in bradycardia can contribute to heart failure that can be corrected with conventional bradycardia pacing. Also, some CHF patients suffer from some degree of AV block such that their cardiac output is improved by synchronizing atrial and ventricular contractions with dual-chamber pacing using a programmed AV delay time (i.e., atrial triggered ventricular pacing or AV sequential pacing).

CHF patients may also suffer from conduction defects of the specialized conduction system of the heart (a.k.a. bundle branch blocks) so that a depolarization impulse from the AV node reaches one ventricle before the other. Stretching of the ventricular wall brought about by CHF can also cause slowed conduction of depolarization impulses through the ventricle. If conduction velocity is slowed in the left ventricle more than the right, for example, the contraction of the two ventricles during ventricular systole becomes uncoordinated which lessens pumping efficiency. In both of these situations, cardiac output can be increased by improving the synchronization of right and left ventricular contractions.

Cardiac pacemakers have therefore been developed which provide pacing to both ventricles. For example, any device of the present invention may incorporate features of one or more of the following references: U.S. Pat. No. 4,928,688, commonly owned U.S. Pat. No. 7,260,432 and U.S. Pat. Nos. 6,411,848; 6,285,907; 6,459,929; 5,334,222; 6,026,320; 6,371,922; 6,597,951; 6,424,865; and 6,542,775, each of which is hereby incorporated herein by reference.

The specialized His-Purkinje conduction network of the heart rapidly conducts excitatory impulses from the sinoatrial node to the atrioventricular node, and then to the ventricular myocardium to result in a coordinated contraction of both ventricles. Artificial pacing with an electrode fixed into an area of the myocardium does not take advantage of the heart's normal specialized conduction system for conducting excitation throughout the ventricles. This is because the specialized conduction system can only be entered by impulses emanating from the atrioventricular node. Thus, the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode. Although the pumping efficiency of the heart is somewhat reduced from the optimum, most patients can still maintain more than adequate cardiac output with artificial pacing.

In multi-site pacing, the atria and/or ventricles are paced at more than one site in order to effect a spread of excitation that results in a more coordinated contraction. Biventricular pacing, as described above, is one example of multi-site pacing in which both ventricles are paced in order to synchronize their respective contractions. Multi-site pacing may also be applied to only one chamber. For example, a ventricle may be paced at multiple sites with excitatory stimulation pulses in order to produce multiple waves of depolarization that emanate from the pacing sites. This may produce a more coordinated contraction of the ventricle and thereby compensate for intraventricular conduction defects that may exist. Stimulating one or both ventricles with multi-site pacing in order to improve the coordination of the contractions and overcome interventricular or intraventricular conduction defects is termed resynchronization therapy.

Altering the coordination of ventricular contractions with multi-site pacing can also be used to deliberately change the distribution of wall stress experienced by the ventricle during the cardiac pumping cycle. The degree to which a heart muscle fiber is stretched before it contracts is termed the preload. The maximum tension and velocity of shortening of a muscle fiber increases with increasing preload. The increase in contractile response of the heart with increasing preload is known as the Frank-Starling principle. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region that contracts later than other regions is subjected to both an increased preload and afterload. This situation is created frequently by the ventricular conduction delays associated with heart failure and ventricular dysfunction.

The heart's initial physiological response to the uneven stress resulting from an increased preload and afterload is compensatory hypertrophy in those later contracting regions of the myocardium. In the later stages of remodeling, the regions may undergo atrophic changes with wall thinning due to the increased stress. The parts of the myocardium that contract earlier in the cycle, on the other hand, are subjected to less stress and are less likely to undergo hypertrophic remodeling. The present invention makes use of this phenomena in order to effect reversal of remodeling by pacing one or more sites in a ventricle (or an atrium) with one or more excitatory stimulation pulses during a cardiac cycle with a specified pulse output sequence. The pace or paces are delivered in a manner that excites a previously stressed and remodeled region of the myocardium earlier during systole so that it experiences less afterload and preload. This pre-excitation of the remodeled region relative to other regions unloads the region from mechanical stress and allows reversal of remodeling to occur.

In another application of the invention, pre-excitation stimulation may be used to unload a stressed myocardial region that has been weakened by ischemia or other causes. Such regions of the myocardium may be particularly vulnerable to dilation and formation of aneurysms. An increased preload and afterload also requires an increased energy expenditure by the muscle which, in turn, increases its perfusion requirements and may result in further ischemia. Pre-excitation of an ischemic region may thus reduce the region's need for blood as well as reduce the mechanical stress to which the region is subjected during systole to reduce the likelihood of further dilation.

A block diagram of a cardiac rhythm management device suitable for practicing the present invention is shown in FIG. 1. The controller of the device is made up of a microprocessor 10 communicating with a memory 12 via a bidirectional data bus, where the memory 12 typically includes a ROM (read-only memory) for program storage and a RAM (random-access memory) for data storage. The controller could also include dedicated circuitry either instead of, or in addition to, the programmed microprocessor for controlling the operation of the device. The device has atrial sensing/stimulation channels including electrode 34, lead 33, sensing amplifier 31, pulse generator 32, and an atrial channel interface 30 which communicates bi-directionally with a port of microprocessor 10. The device also has multiple ventricular sensing/stimulation channels for delivering multi-site univentricular or biventricular pacing. Two such ventricular channels are shown in the figure that include electrodes 24a-b, leads 23a-b, sensing amplifiers 21a-b, pulse generators 22a-b, and ventricular channel interfaces 20a-b where "a" designates one ventricular channel and "b" designates the other. For each channel, the same lead and electrode may be used for both sensing and stimulation. The channel interfaces 20a-b and 30 may include analog-to-digital converters for digitizing signal inputs from the sensing amplifiers and registers which can be written to by the microprocessor in order to output stimulation pulses, change the stimulation pulse amplitude, and adjust the gain and threshold values for the sensing amplifiers. A telemetry interface 40 is provided for communicating with an external programmer.

The controller is capable of operating the device in a number of programmed pacing modes that define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. Rate-adaptive pacing modes can also be employed where the ventricular and/or atrial escape intervals are modulated based upon measurements corresponding to the patient's exertion level.

As shown in FIG. 1, an activity level sensor 52 (e.g., a minute ventilation sensor or accelerometer) provides a measure of exertion level to the controller for pacing the heart in a rate-adaptive mode. Multiple excitatory stimulation pulses can also be delivered to multiple sites during a cardiac cycle in order to both pace the heart in accordance with a bradycardia mode and provide resynchronization of contractions to compensate for conduction defects. In accordance with the invention, the controller may also be programmed to deliver stimulation pulses in a specified pulse output sequence in order to effect reduction of stress to a selected myocardial region.

Figure 2:
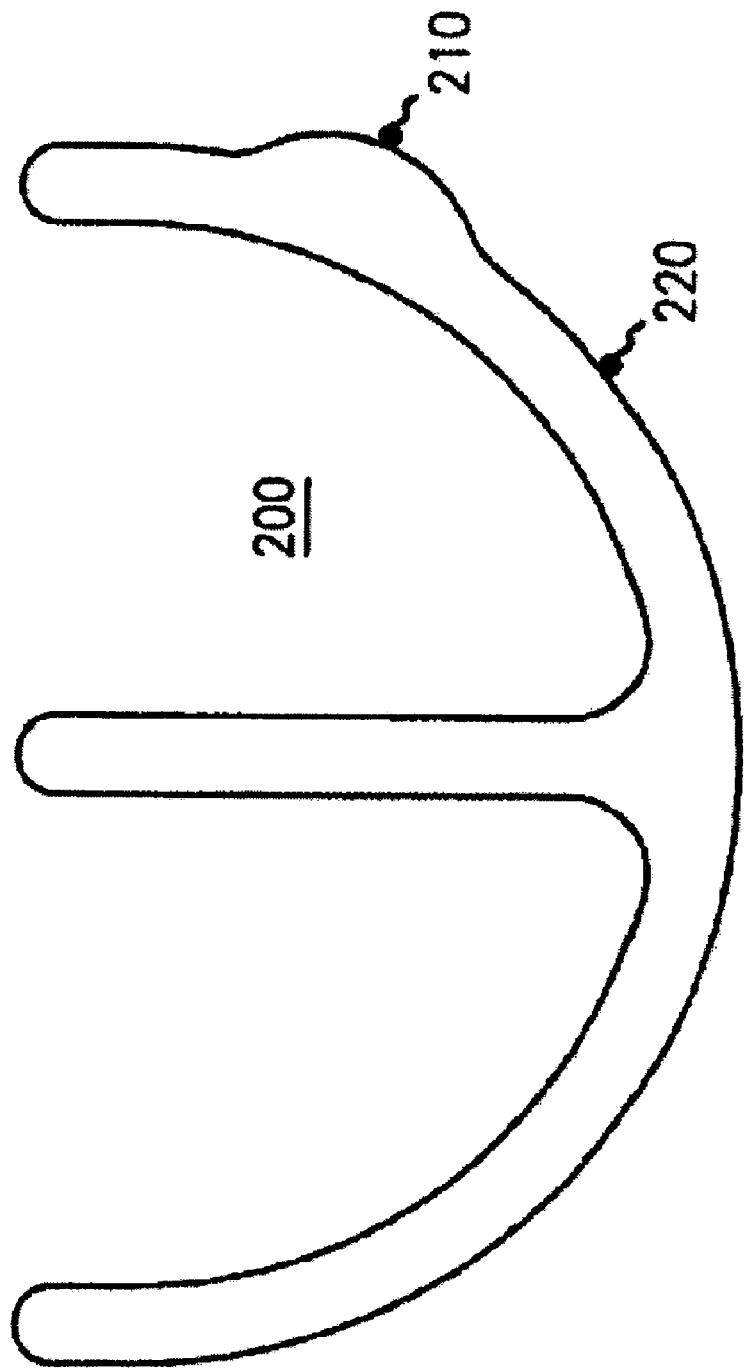
FIGS. 2 and 3 are diagrams showing examples of sensing/pacing electrode placement according to embodiments of the present invention.
Figure 3:
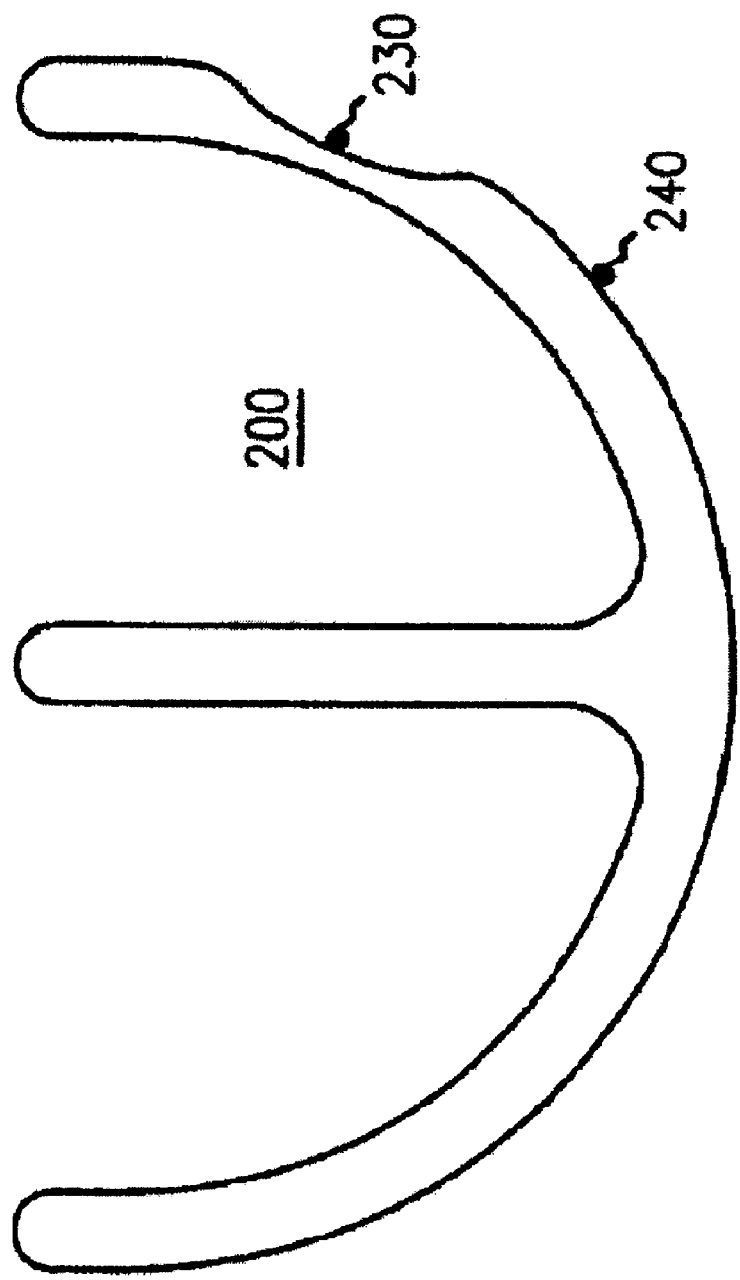

Methods and devices in accordance with the present invention may be beneficially employed to unload a stressed myocardial region that is either hypertrophied or thinned. FIG. 2 depicts a left ventricle 200 with pacing sites 210 and 220 to which may be fixed epicardial stimulation/sensing electrodes. The myocardium at pacing site 210 is shown as being hypertrophied as compared to the myocardium at pacing site 220. A cardiac rhythm management device such as shown in FIG. 1 may deliver stimulation pulses to both sites in accordance with a pacing mode through its ventricular stimulation/sensing channels. In order to unload the hypertrophied site 210 during systole and thereby promote reversal of the hypertrophy, the ventricle is paced with a pulse output sequence that stimulates the hypertrophied site 210 before the other site 220. The lessened mechanical stress during systole then allows the site 210 to undergo reversal of the hypertrophy. FIG. 3 shows a left ventricle 200 in which the pacing site 240 is relatively normal while the site 230 is a myocardial region that has been thinned due to late state remodeling or other stresses such as ischemia. Again, pacing of the ventricle with pre-excitation stimulation of site 230 relative to the site 240 unloads the thinned region and subjects it to less mechanical stress during systole. The result is either reversal of the remodeling or reduction of further wall thinning.

In one embodiment, a pre-excitation stimulation pulse is applied to a stressed region either alone or in a timed relation to the delivery of a stimulation pulse applied elsewhere to the myocardium. For example, both the right and left ventricles can be paced at separate sites by stimulation pulses delivered with a specified interventricular delay between the pulses delivered to each ventricle. By adjusting the interventricular delay so that one of the ventricular pacing sites is pre-excited relative to the other, the spread of activation between the two pacing sites can be modified to change the wall stresses developed near these sites during systolic contraction. Other embodiments may employ multiple electrodes and stimulation channels to deliver pulses to multiple pacing sites located in either of the atria or the ventricles in accordance with a specified pulse output sequence. A multi-site pacemaker may also switch the output of pacing pulses between selected electrodes or groups of electrodes during different cardiac cycles. Pacing is then delivered to a heart chamber through a switchable configuration of pacing electrodes, wherein a pulse output configuration is defined as a specific subset of two or more electrodes fixed to the paced chamber and to which pacing pulses are applied as well as the timing relations between the pulses. Two or more different pulse output configurations may be defined as subsets of electrodes that can be selected for pacing. By switching the pulse output configuration to a different configuration, pacing to the heart chamber is thereby temporally distributed among the total number of fixed electrodes. The principle remains the same in these embodiments, however, of unloading a stressed myocardial site by pre-exciting it relative to other regions of the myocardium.

In other embodiments, a stressed region of the ventricular myocardium is pre-excited in a timed relation to a triggering event that indicates an intrinsic beat has either occurred or is imminent. For example, a pre-excitation stimulation pulse may be applied to a stressed region immediately following the earliest detection of intrinsic activation elsewhere in the ventricle. Such activation may be detected from an electrogram with a conventional ventricular sensing electrode. An earlier occurring trigger event may be detected by extracting the His-Purkinje bundle conduction potential from a special ventricular sensing electrode using signal-processing techniques.

In order to deliver a pre-excitation stimulus to a stressed site at a time well before any intrinsic activation takes place at other sites, the stimulus can be applied after a specified AV delay interval following an atrial sense or atrial pace. The objective in this situation is to deliver the pre-excitation stimulus before the excitation from the atrio-ventricular node reaches the ventricles via the specialized conduction pathway. Accordingly, the normal intrinsic atrio-ventricular delay (e.g., the PR interval on an EKG or the equivalent electrogram interval recorded using implanted leads) can be measured, with the AV pacing delay interval then programmed to be shorter than the measured intrinsic AV delay interval by a specified pre-excitation interval. The AV pacing delay interval may be either fixed at some value (e.g., at 60 ms, with a variable range of 0-150 ms) or be made to vary dynamically with a measured variable such as heart rate or exertion level.

The AV pacing delay interval for delivering a pre-excitation stimulus following an atrial sense or pace may also be set in accordance with a measured intrinsic conduction delay interval between the site to be pre-excited and another ventricular site, referred to as a V-V interval. The objective in this case is to reverse the intrinsic conduction delay existing between the two sites by pacing with a similar delay of opposite sign. For example, the intrinsic conduction delay between a stressed ventricular site and an earlier excited site is measured. The stressed site is then pre-excited after an AV pacing delay interval following an atrial sense or pace that is set in accordance with the measured V-V interval. In one embodiment, the pre-excitation interval is set as a linear function of the V-V interval:

Pre-excitation interval=$(a)(V\text{-}V\text{ interval})+b$

The AV pacing delay interval is then computed by subtracting the pre-excitation interval from the measured intrinsic AV delay interval.

A clinician may use various techniques in order to determine areas that have undergone remodeling or are otherwise stressed. For example, ventricular wall thickness abnormalities and regional variations in myocardial mass may be observed with echocardiography or magnetic resonance imaging. Observation of akinetic or dyskinetic regions of the ventricle during contraction with an appropriate imaging modality may also be used to indicate stressed regions. Coronary angiograms indicating blood flow abnormalities and electrophysiological studies indicating regions of ischemia or infarction may be used to identify regions that have been stressed due to ischemia. Electrophysiological studies may also be used to determine regional conduction delays that can be reversed with pre-excitation stimulation. The pulse output sequence of a multi-site pacemaker or the interventricular delay of a biventricular pacemaker may then be initially specified in accordance with those findings so that stressed regions are excited first during a paced cardiac cycle.

In a further refinement, an implanted cardiac rhythm management device may automatically adjust the pulse output sequence in accordance with measurements of myocardial mass. Such measurements may be made by measuring the conduction delays of excitation spreading through the myocardium as sensed by multiple sensing/stimulation electrodes. Increased conductions delays through a region, for example, may be reflective of stress in the region that can be reduced by pre-excitation stimulation. In another embodiment, impedance measurements may be made between electrodes in proximity to the heart that correlate with variations in myocardial mass and contraction sequence. Such measurements may be used to identify akinetic or dyskinetic regions of the myocardium as well as to indicate wall thickness abnormalities. The particular pre-excitation interval used by the device may also be automatically adjusted in accordance with detected changes in the remodeling process. That is, the pre-excitation interval may be shortened as remodeling is reversed or increased as remodeling worsens. Remodeling changes can be detected by, for example, measuring changes or trends in conduction delays, contraction sequences, end-diastolic volume, stroke volume, ejection fraction, wall thickness, or pressure measurements.

In another embodiment, the pulse output sequence used by a cardiac rhythm management may be alternated between one designed to produce hemodynamically more effective contractions when metabolic needs of the body are great to one designed to promote reverse remodeling when metabolic needs are less. A pulse output sequence that unloads a hypertrophic region may not be the optimum pulse output sequence for maximizing hemodynamic performance. For example, a more hemodynamically effective contraction may be obtained by exciting all areas of the myocardium simultaneously, which may not effectively promote reversal of the hypertrophy or remodeling. The pulse output sequence may therefore be adjusted automatically in accordance with exertion level measurements reflective of metabolic demand so that pulse output sequences that unload hypertrophied or stressed regions are not used during periods of increased exertion.

Figure 4A:
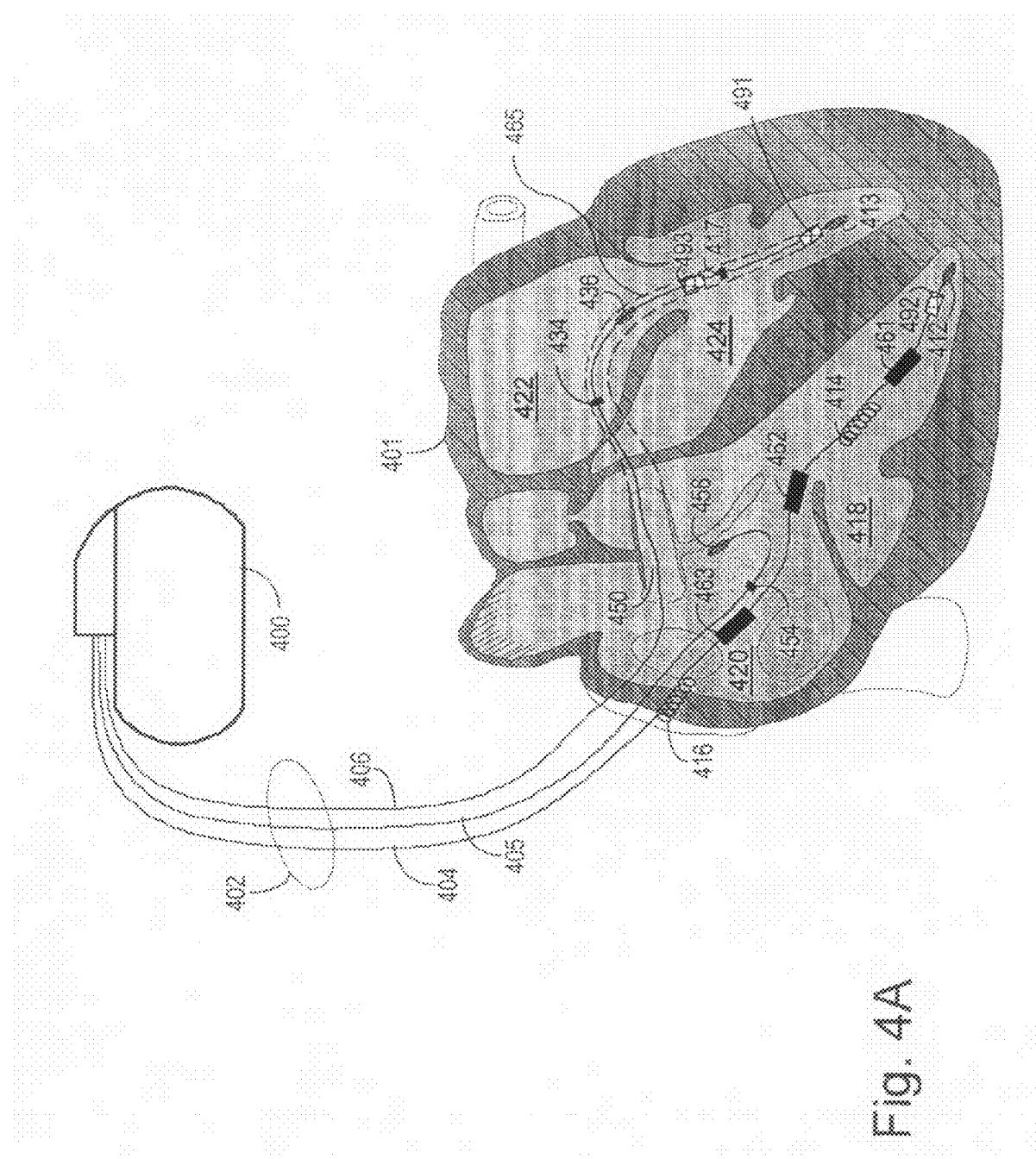
FIG. 4A is an illustration of an implantable cardiac device including a lead assembly shown implanted in a sectional view of a heart, the device configured for ventricular wall remodeling reversal in accordance with embodiments of the present invention.

Referring to FIG. 4A, there is shown a body implantable device that represents one of several types of devices with implantable leads that may be used to reverse remodeling of the ventricular wall in accordance with embodiments of the present invention. For example, a patient internal medical device (PIMD) 400, illustrated in FIG. 4A as a pacemaker/defibrillator, may be representative of all or part of a pacemaker, defibrillator, cardioverter, cardiac monitor, or re-synchronization device (e.g., multichamber or multisite device).

The implantable device illustrated in FIG. 4A is an embodiment of the PIMD 400 including an implantable pacemaker/defibrillator electrically and physically coupled to an intracardiac lead system 402. The intracardiac lead system 402 is implanted in a human body with portions of the intracardiac lead system 402 inserted into a heart 401. Electrodes of the intracardiac lead system 402 may be used to detect and analyze cardiac signals produced by the heart 401 and to provide stimulation and/or therapy energy to the heart 401 under predetermined conditions, to treat cardiac arrhythmias of the heart 401.

The PIMD 400 depicted in FIG. 4A is a multi-chamber device, capable of sensing signals from one or more of the right and left atria 420, 422 and the right and left ventricles 418, 424 of the heart 401 and providing pacing pulses to one or more of the right and left atria 420, 422 and the right and left ventricles 418, 424. Low energy pacing pulses may be delivered to the heart 401 to regulate the heartbeat for remodeling reversal, for example. In a configuration that includes cardioversion/defibrillation capabilities, high-energy pulses may also be delivered to the heart 401 if an arrhythmia is detected that requires cardioversion or defibrillation.

The intracardiac lead system 402 includes a right ventricular lead system 404, a right atrial lead system 405, and a left atrial/ventricular lead system 406. The right ventricular lead system 404 includes an RV-tip pace/sense electrode 412, an RV-coil electrode 414, and one or more electrodes 461, 462, 463 suitable for measuring transthoracic impedance. In one arrangement, impedance sense and drive electrodes 461, 462, 463 are configured as ring electrodes. The impedance drive electrode 461 may be located, for example, in the right ventricle 418. The impedance sense electrode 462 may be located in the right atrium 420. Alternatively or additionally, an impedance sense electrode 463 may be located in the superior right atrium 420 or near the right atrium 420 within the superior vena cava.

The RV-tip electrode 412 is positioned at an appropriate location within the right ventricle 418 for pacing the right ventricle 418 and sensing cardiac activity in the right ventricle 418. The right ventricular lead system may also include one or more defibrillation electrodes 414, 416, positioned, for example, in the right ventricle 418 and the superior vena cava, respectively.

The atrial lead system 405 includes A-tip and A-ring cardiac pace/sense electrodes 456, 454. In the configuration of FIG. 4A, the intracardiac lead system 402 is positioned within the heart 401, with a portion of the atrial lead system 405 extending into the right atrium 420. The A-tip and A-ring electrodes 456, 454 are positioned at an appropriate location within the right atrium 420 for pacing the right atrium 420 and sensing cardiac activity in the right atrium 420.

The lead system 402 illustrated in FIG. 4A also includes a left atrial/left ventricular lead system 406. The left atrial/left ventricular lead system 406 may include, one or more electrodes 434, 436, 417, 413 positioned within a coronary vein 465 of the heart 401. Additionally, or alternatively, one or more electrodes may be positioned in a middle cardiac vein, a left posterior vein, a left marginal vein, a great cardiac vein or an anterior vein.

The left atrial/left ventricular lead system 406 may include one or more endocardial pace/sense leads that are advanced through the superior vena cava (SVC), the right atrium 420, the valve of the coronary sinus, and the coronary sinus 450 to locate the LA-tip 436, LA-ring 434, LV-tip 413 and LV-ring 417 electrodes at appropriate locations adjacent to the left atrium 422 and left ventricle 424, respectively. In one example, lead placement involves creating an opening in a percutaneous access vessel, such as the left subclavian or left cephalic vein. For example, the lead system 402 may be guided into the right atrium 420 of the heart via the superior vena cava.

From the right atrium 420, the left atrial/left ventricular lead system 406 is deployed into the coronary sinus ostium, the opening of the coronary sinus 450. The left atrial/left ventricular lead system 406 is guided through the coronary sinus 450 to a coronary vein of the left ventricle 424. This vein is used as an access pathway for leads to reach the surfaces of the left atrium 422 and the left ventricle 424 which are not directly accessible from the right side of the heart. Lead placement for the left atrial/left ventricular lead system 406 may be achieved via subclavian vein access. For example, a preformed guiding catheter may be used for insertion of the LV and LA electrodes 413, 417, 436, 434 adjacent the left ventricle 424 and left atrium 422, respectively.

Lead placement for the left atrial/left ventricular lead system 406 may be achieved via the subclavian vein access and a preformed guiding catheter for insertion of the LV and LA electrodes 413, 417, 436, 434 adjacent the left ventricle 424 and left atrium 422, respectively. In one configuration, the left atrial/left ventricular lead system 406 is implemented as a single-pass lead. It is understood that the descriptions in the preceding paragraphs with regard to LV-tip 413 and LV-ring 417 electrodes are equally applicable to a lead configuration employing distal and proximal LV ring electrodes (with no LV-tip electrode).

Additional configurations of sensing, pacing and defibrillation electrodes may be included in the intracardiac lead system 402 to allow for various sensing, pacing, remodeling reversal, and defibrillation capabilities of multiple heart chambers. In other configurations, the intracardiac lead system 402 may have only a single lead with electrodes positioned in the right ventricle to implement single chamber cardiac pacing. In yet other embodiments, the intracardiac lead system 402 may not include the left atrial/left ventricular lead 406 and may support pacing and sensing of the right atrium and right ventricle only. Any intracardiac lead and electrode arrangements and configurations may be implanted within the scope of the present system in accordance with embodiments of the invention.

The PIMD 400 may include one or more sensors configured to detect local wall motion, velocity, and/or stress. For example, one or more accelerometers 491, 493 may be used to monitor local heart wall movement. This information can be used in closed loop fashion to control therapy by changing the pacing site (if multiple electrodes are available) or timing. A strain gauge 492 may alternately or additionally be used to detect flexing that occurs due to the local contraction of the ventricular wall. The strain gauge 492 and/or the accelerometers 491,493 may be provided in or on the intracardiac lead system 402 at a variety of locations. For example, the strain gauge 492 and/or the accelerometer 491 may be provided proximate the LV electrode 413, proximate the LV electrode 436, proximate the RV electrode 412, or at other locations suitable for determining local wall stress relative to a pace electrode. The strain gauge 492 and/or the accelerometers 491,493 may be of varying type, including, but not limited to, micro-electro-mechanical systems (MEMS) sensors.

PIMD 400 may be configured to treat problems in accordance with the present invention, such as by providing electrical pacing stimulation to one or both ventricles in an attempt to reverse remodeling of the ventricular wall to improve the coordination of ventricular contractions. The PIMD 400 may be configured structurally and functionally in a manner described in commonly owned U.S. Pat. Nos. 6,597, 951; 6,574,506; 6,512,952; 6,501,988; 6,411,848; and 6,363, 278, each of which is hereby incorporated herein by reference.

Referring now to FIG. 4B, the PIMD 400 is illustrated as including a mesh 481 configured for local measurements of the cardiac wall. The mesh 481 is coupled to the PIMD 400 using a cable 482. The mesh 481 may be configured as an (x,y) coordinate grid, where each vertical mesh element and each horizontal mesh element intersect at a node of the (x,y) coordinate system. For example, a node 483 is identified on the mesh 481 at the intersection of the third horizontal and third vertical mesh elements, if mesh elements are numbered starting at the upper left corner of the mesh 481 as illustrated in FIG. 4B. The node 483 would then correspond to the (x,y) coordinate (3,3). Each node may thus be associated with a strain measurement capability useful for local cardiac wall stress calculations.

Figure 5:
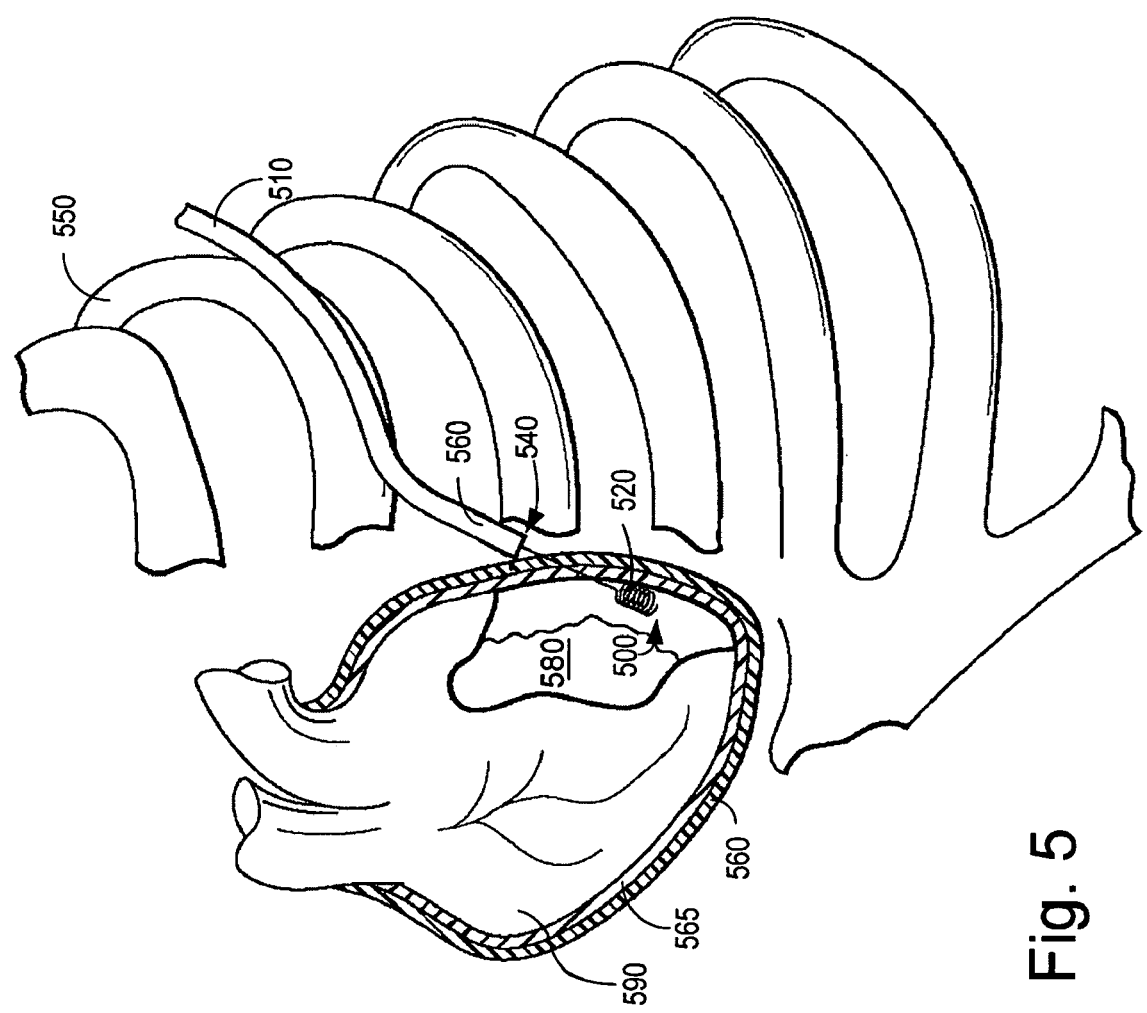
FIG. 5 illustrates an epicardial lead having a helical fixation arrangement in the myocardium for ventricular wall remodeling reversal in accordance with an embodiment of the present invention.

FIG. 5 illustrates embodiments of the present invention using epicardial leads for cardiac remodeling reversal. FIG. 5 illustrates a patient's heart 590 in a cut-away view through the rib-cage 550. A lead 510 having a helical electrode 520 is implanted in a myocardium 580 in accordance with an embodiment of the present invention. During delivery of the lead 510, the electrode 520 is implanted within the myocardium 580 by rotating the lead 510. In another embodiment, the electrode 520 may be inserted into the myocardium 580 and actively extended out from the lead and into myocardial tissue.

In a fixed electrode arrangement, as the lead 510 is rotated, the sharp end 500 of the helical electrode 520 penetrates through an epicardium 560, through an epicardial space 565, and penetrates into the myocardium 580. As the lead 510 is further rotated, the sharp end 500 burrows through the tissue, penetrating further into myocardial tissue and acutely fixing the electrode within the myocardium 580. This process effectively screws the helical electrode 520 into the myocardial tissue.

The lead 510 may be affixed at a location pre-determined to have an abnormal wall stress, and/or the lead 510 may include one or more sensors, such as an acceleration sensor, a strain sensor, an ultrasonic velocity sensor, or other local stress sensor, to determine abnormal wall stress locations. For example, the helical electrode 520 may incorporate stress measurement capabilities by acting as a strain-gage, useful for determining local wall stress abnormalities after implantation. Optionally or additionally, the lead 510 may incorporate sensors capable of determining local wall stress, such as by using localized ultrasonic Doppler velocimetry. Leads incorporating ultrasonic Doppler systems are further described in commonly owned U.S. patent application Ser. No. 10/930,088 entitled "Sensor Guided Epicardial Lead," filed on Aug. 31, 2004, which is hereby incorporated herein by reference.

Local wall stress abnormalities may be pre-determined prior to lead placement. For example, electrodes may be built into the mesh of a cardiac support device, such as the COR-CAP, a trademarked device available from Acorn Cardiovascular Inc. in St. Paul, Minn., USA. Electrodes may be positioned about the heart on the epicardial surface and may be used for sensing delays in electrical activation. If, alternately or additionally, strain gauges are positioned at various points in the mesh of a CORCAP type device, delays in mechanical activation of the heart may be monitored. This would be one way to monitor mechanical dysnchrony and/or to determine wall stress abnormalities.

Figure 6:
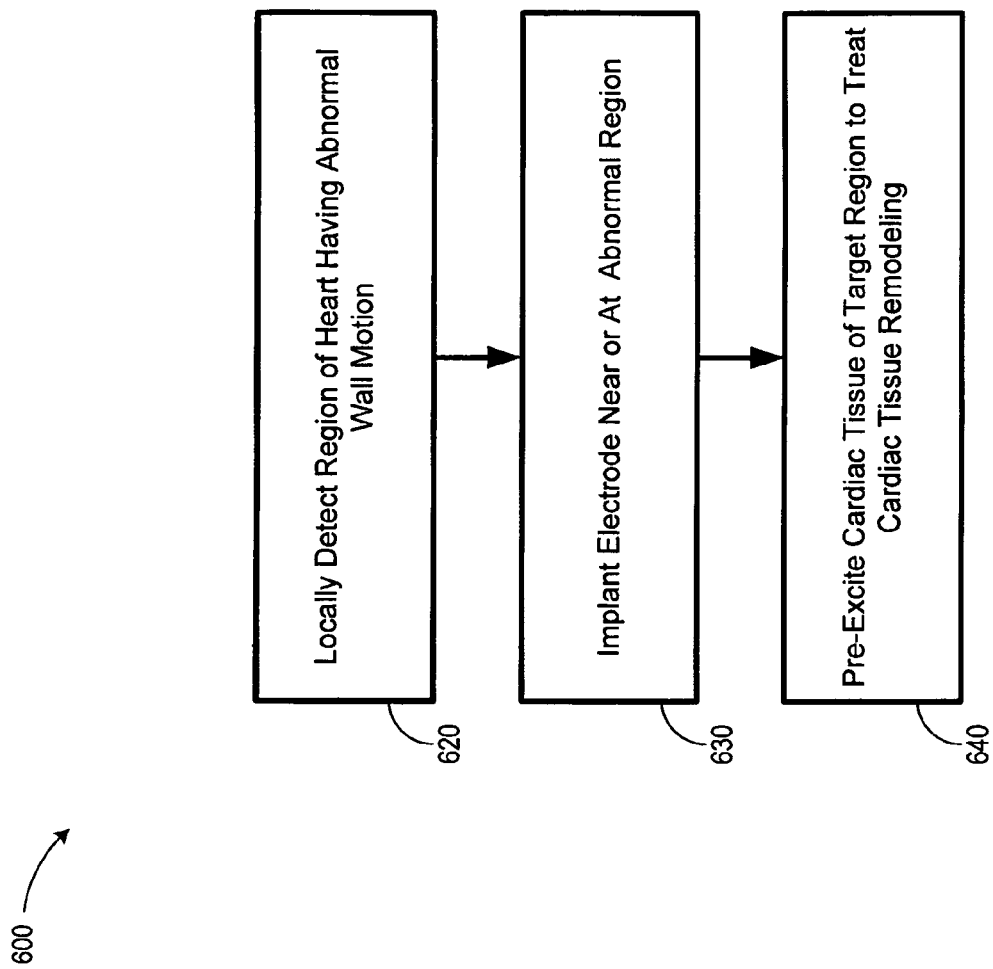
FIG. 6 is a flow chart directed to methods of cardiac tissue remodeling reversal in accordance with the present invention.

Referring now to FIG. 6, a method 600 of cardiac remodeling reversal in accordance with the present invention involves detecting 620, proximate the heart wall, a target region having a level of abnormal wall motion relative to neighboring regions. An electrode is implanted 630 near or at the target region. The target region is pre-excited 640 relative to the neighboring regions of the heart wall using the electrode in order to alter stress at the target region for treating cardiac tissue remodeling.

Heart wall motion 620 may be detected using, for example, an acceleration measurement, a strain measurement, and an ultrasonic velocity measurement such as a local Doppler tissue velocity measurement. The electrode may be used to pre-excite 640 the target region in response to an atrial sense, an atrial pace, a ventricular sense or pace event, or other timing methodology. The remodeling reversal pre-excitation 640 may be adjusted in accordance with activity level measurements reflective of metabolic demand. Detecting 620 the target region of the heart may involve sensing activation characteristics of heart wall tissue, such as one or more electrophysiologic characteristics, complex impedance characteristics, or other characteristics of the heart wall tissue indicative of remodeling.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A lead implantation method, comprising:
   accessing a heart of a patient, the heart having a heart wall;
   detecting, proximate the heart wall, a target region of the heart wall having a level of abnormal wall motion relative to neighboring regions of the heart wall;
   implanting an electrode of the lead at the target region;
   pre-exciting the target region relative to the neighboring regions of the heart wall using the lead electrode in order to alter stress at the target region for treating cardiac remodeling; and
   adjusting the pre-excitation in accordance with activity level measurements reflective of metabolic demand.

2. The method of claim 1, wherein the wall motion is detected using an acceleration measurement.

3. The method of claim 1, wherein the wall motion is detected using a strain measurement.

4. The method of claim 1, wherein the wall motion is detected using an ultrasonic velocity measurement.

5. The method of claim 1, wherein accessing the patient's heart comprises accessing an epicardial surface of the patient's heart.

6. The method of claim 1, wherein accessing the patient's heart comprises accessing an endocardial surface of the patient's heart.

7. The method of claim 1, wherein accessing the patient's heart comprises accessing the patient's heart through one or more vessels of the patient's upper venous system.

8. The method of claim 1, wherein detecting the target region comprises sensing activation characteristics of heart wall tissue at a plurality of heart wall sites.

9. The method of claim 1, wherein detecting the target region comprises detecting one or more electrophysiologic characteristics of heart wall tissue.

10. The method of claim 1, wherein detecting the target region comprises detecting complex impedance characteristics of heart wall tissue.

11. A cardiac system, comprising:
an implantable housing;
a controller provided in the housing and configured to control cardiac monitoring and cardiac stimulation;
detection circuitry provided in the housing and coupled to the controller;
energy delivery circuitry provided in the housing and coupled to the controller; and
a lead coupled to the detection circuitry and the energy delivery circuitry, the lead comprising:
a lead body;
at least one cardiac electrode coupled to the lead body; and
at least one sensor supported by the lead body and configured to detect abnormal cardiac wall motion, the sensor providing information useful for positioning the cardiac electrode proximate a target heart wall location associated with increased stress relative to neighboring heart wall locations;
wherein the controller is configured to coordinate delivery of a pre-excitation stimulus to the target heart wall location using the cardiac electrode in order to alter stress at the target region for treating cardiac remodeling, and the controller is also configured to adjust the pre-excitation stimulus in accordance with activity level measurements reflective of metabolic demand.

12. The system of claim 11, wherein the sensor is situated at a distal region of the lead.

13. The system of claim 11, wherein the sensor comprises an accelerometer.

14. The system of claim 11, wherein the sensor comprises a strain gauge.

15. The system of claim 11, wherein the sensor comprises an ultrasonic velocimeter.

16. The system of claim 11, wherein the sensor is supported within a lumen of the lead.

17. The system of claim 11, wherein the controller coordinates delivery of the pre-excitation stimulus to the target heart wall location prior to an intrinsic conduction or delivery of a pace pulse.

18. The system of claim 11, further comprising:
an activity sensor situated in or on the housing and coupled to the controller to provide the activity level measurements.

19. A cardiac system, comprising:
an implantable lead having a lead electrode and adapted to access a heart of a patient, the heart having a heart wall;
means for detecting, proximate the heart wall, a target region of the heart wall having a level of abnormal wall motion relative to neighboring regions of the heart wall;
means for pre-exciting the target region relative to the neighboring regions of the heart wall using the lead electrode in order to alter stress at the target region for treating cardiac remodeling; and
means for adjusting the pre-excitation in accordance with activity level measurements reflective of metabolic demand.

20. The system of claim 19, wherein the implantable lead comprises at least one sensor coupled to the detecting means and configured to sense the abnormal cardiac wall motion.

21. The system of claim 20, further comprising an activity sensor coupled to the controller to provide the activity level measurements.

* * * * *

UNITED STATES PATENT AND TRADEMARK OFFICE
CERTIFICATE OF CORRECTION

PATENT NO. : 7,725,185 B2
APPLICATION NO. : 12/070080
DATED : May 25, 2010
INVENTOR(S) : Liu et al.

Page 1 of 1

It is certified that error appears in the above-identified patent and that said Letters Patent is hereby corrected as shown below:

In the Specification:

Col. 3, line 9: "following and" should read --following detailed description and--.

Signed and Sealed this

Fourteenth Day of September, 2010

David J. Kappos
*Director of the United States Patent and Trademark Office*